(12) United States Patent
Desmond, III et al.

(10) Patent No.: US 6,770,101 B2
(45) Date of Patent: Aug. 3, 2004

(54) PROSTATIC STENT AND DELIVERY SYSTEM

(75) Inventors: Joseph P. Desmond, III, Bloomington, IN (US); James A. Teague, Spencer, IN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/973,562

(22) Filed: Oct. 9, 2001

(65) Prior Publication Data

US 2003/0069647 A1 Apr. 10, 2003

(51) Int. Cl.⁷ .................................................. A61F 2/36
(52) U.S. Cl. .............................. 623/23.66; 623/23.64
(58) Field of Search .................. 604/8, 104; 623/1.18, 623/1.2, 1.3, 1.31, 1.34, 1.46, 23.64, 23.66, 23.7; 600/29, 30; 606/108, 153, 191, 194, 195

(56) References Cited

U.S. PATENT DOCUMENTS

| | | | |
|---|---|---|---|
| 4,434,797 A | 3/1984 | Silander | |
| 4,655,771 A | 4/1987 | Wallsten | 623/1 |
| 4,762,128 A | 8/1988 | Rosenbluth | 128/343 |
| 4,911,687 A | 3/1990 | Stewart et al. | 604/15 |
| 4,946,449 A | 8/1990 | Davis, Jr. | 604/256 |
| 4,955,859 A | 9/1990 | Zilber | 604/8 |
| 4,978,341 A | 12/1990 | Niederhauser | 604/167 |
| 4,994,066 A | 2/1991 | Voss | |
| 5,123,917 A | 6/1992 | Lee | |
| 5,246,445 A | 9/1993 | Yachia et al. | 606/108 |
| 5,269,802 A | 12/1993 | Garber | 606/191 |
| 5,356,423 A | 10/1994 | Tihon et al. | 606/194 |
| 5,391,196 A | 2/1995 | Devonec | 607/96 |
| 5,514,176 A | 5/1996 | Bosley, Jr. | 623/1 |
| 5,518,498 A | 5/1996 | Lindenberg et al. | |
| 5,601,591 A | 2/1997 | Edwards et al. | 606/198 |
| 5,667,486 A | 9/1997 | Mikulich et al. | 604/8 |
| 5,766,209 A | 6/1998 | Devonec | 604/8 |
| 5,782,855 A | 7/1998 | Lau et al. | 606/194 |
| 5,928,217 A | 7/1999 | Mikus et al. | 604/530 |
| 5,964,771 A | 10/1999 | Beyar et al. | 606/108 |
| 5,968,052 A | 10/1999 | Sullivan, III et al. | 606/108 |
| 6,019,744 A | 2/2000 | Altdorf et al. | 604/16 |

(List continued on next page.)

FOREIGN PATENT DOCUMENTS

| | | |
|---|---|---|
| DE | 197 13 280 A1 | 10/1998 |
| EP | 1 110 561 A2 | 6/2001 |
| FR | 2 767 673 A1 | 3/1999 |
| SU | 1 412 774 A1 | 7/1988 |
| WO | WO 00/44308 | 8/2000 |

OTHER PUBLICATIONS

Copy of International Search Report for International Patent Application No. PCT/US02/31723, mailed from the International Search Authority on Jan. 13, 2004.

(List continued on next page.)

*Primary Examiner*—Corrine McDermott
*Assistant Examiner*—William H Matthews
(74) *Attorney, Agent, or Firm*—Testa, Hurwitz & Thibeault, LLP

(57) ABSTRACT

A collapsible and expandable stent includes a body segment, first and second terminal ends spaced apart from each other, a substantially smooth wall and a lumen extending between the first and second ends. The device can be used for maintaining the patency of the prostatic urethra in a male patient. The stent may be designed according to the individual needs of particular patients. A delivery system for deploying the stent and other collapsible and expandable stents in the body of the patient comprises a retractable sheath, a shaft and a locking element to reversibly lock the sheath to the shaft.

31 Claims, 14 Drawing Sheets

U.S. PATENT DOCUMENTS

| | | |
|---|---|---|
| 6,033,413 A | 3/2000 | Mikus et al. ............... 606/108 |
| 6,146,415 A | 11/2000 | Fitz ........................... 623/1.11 |
| 6,162,231 A | 12/2000 | Mikus et al. ............... 606/108 |
| 6,168,617 B1 | 1/2001 | Blaeser et al. ............. 623/1.11 |
| 6,270,523 B1 | 8/2001 | Herwecket et al. |

OTHER PUBLICATIONS

Stoeckel et al., "Superelastic Ni–Ti Wire", *Wire Journal International*, pp. 45–50, Mar. 1991.

Teague et al., 09/829,705, "Reinforced Retention Structures", Filed Apr. 10, 2001.

PROSTATIC STENT AND DELIVERY SYSTEM

TECHNICAL FIELD

This invention relates to stents used to maintain a body lumen, such as the prostatic urethra, and to systems for delivering stents into these body lumens.

BACKGROUND INFORMATION

Stents are a known class of medical device for expanding or maintaining an open lumen or passageway in various body cavities, vessels, or ducts. Stents have been employed, for example, in the urethra, the ureters, the biliary tract, the cervix, the rectum, the esophagus and blood vessels to relieve the pathological effects of constrictions occurring in these passageways.

Bladder obstruction arising from enlargement of the prostate gland in males is one of the most commonly encountered disorders in urology. The prostate gland lies under the bladder and surrounds the passageway known as the prostatic urethra, which transfers fluids from the bladder to the sphincter and ultimately outside the body. An enlarged prostate gland constricts the prostatic urethra leading to a condition known as benign prostatic hyperplasia ("BPH"). BPH causes a variety of obstructive symptoms, including urinary hesitancy, straining to void, decreased size and force of the urinary stream, and in extreme cases, complete urinary retention possibly leading to renal failure. A number of other irritating symptoms may also accompany BPH, including urinary frequency and urgency, nocturnal incontinence, and extreme discomfort.

Known stents used to combat BPH may not ensure patient safety and comfort. Indeed, existing stents, such as wire mesh stents, may become entangled with prostate tissue leading to infection and discomfort. Under such conditions, prostate tissue often penetrates the perforations of the wire mesh stent rendering it difficult, if not impossible, to remove without surgical intervention. Other devices, such as Foley catheters are retained in the bladder by a balloon inflated with sterile water or saline. This necessitates use of a collection bag to catch fluids drained from the bladder, thereby reducing a patient's quality of life. In addition, many stents cannot accommodate unusually or abnormally shaped prostatic urethras or prostatic urethras of varying lengths and widths.

Also, internal forces from involuntary bodily functions (such as peristalsis and other secretory forces, as well as patient movement) may force some stents out of their intended position within the prostatic urethra. For instance, the bladder can exert intense pressure during urination, which tends to expel a stent positioned within the prostatic urethra. It is also possible that normal body motions, such as walking or running may displace a stent at this location.

SUMMARY OF THE INVENTION

In one embodiment, the invention reduces the risk of infection/inflammation, while also maintaining patient comfort and preventing migration of the stent out of the prostatic urethra. According to one feature, the outer surfaces of the stent are smooth, and do not become entangled with and/or potentially infect internal body tissue. Structural features of certain embodiments of the invention, including a double funnel or hourglass configuration, ensure that the stent will not dislodge or migrate out of its intended position. According to another feature the stent is easy to insert, and should circumstances warrant, easily removed without the need for invasive surgery. In addition, the stent may be designed according to the individual needs of particular patients by tailoring its dimensions to accommodate prostatic urethras of various sizes and shapes.

One aspect of the invention relates to a collapsible and expandable stent including first and second terminal ends spaced apart from each other, a substantially smooth wall disposed between the first and second terminal ends and a lumen extending between the first and second terminal ends. Preferably, the stent is designed for use in the prostatic urethra of a male patient, and is constructed of flexible biocompatible materials such as elastomeric compounds. Materials like these combine rigidity with the softness necessary for patient stability and comfort. To help retain the stent in place in a body of a patient, at least one of the first and second terminal ends is wider than at least some portion of the wall disposed between the terminal ends.

To further help anchor the stent in the body, the first and second terminal ends may further include a retention ring having an elastic member. Where both the first and second terminal ends include retention rings, these retention rings are preferably aligned in a substantially parallel relationship. By varying the size of the retention rings, the stent can accommodate prostatic urethras of different sizes and shapes. The retention rings may be constructed from the same elastomeric compounds used in the first and second terminal ends. According to one aspect, the rings incorporate an elastic member to provide rigidity to the device and to ensure that the device reverts spontaneously to its predetermined configuration from its collapsed state.

In one embodiment, both the first and second terminal ends are wider than at least some portion of the wall. Under this construction, the wall extending between the terminal ends forms a double funnel or hourglass configuration. Once placed in a patient, this double funnel configuration acts to maintain the stent in position within an open passageway. When placed in the prostatic urethra, for example, one of the first or second terminal ends rests at the bladder end of the prostatic urethra and allows for drainage of urine into the prostatic urethra. The other of the first or second terminal ends sits above the external sphincter to prevent migration into the bulbous urethra while maintaining drainage through the prostate.

A lumen may extend between the first and second terminal ends to allow drainage of fluids through the passageway. Alternatively or additionally, drainage may be provided or enhanced by grooves located on the wall. In addition, the wall may define one or more through-holes disposed along its length to provide for fluid communication with the lumen to further facilitate drainage.

In another embodiment, one of the first and second terminal ends further comprises a dome structure. The dome may define at least one aperture, and terminates in a protuberance. The wall of this embodiment may include at least one annular collar to provide breaking points for the device entering its collapsed state. To further enhance collapsibility, the wall may define one or more slots. The slots may comprise openings through, or concave surfaces along the wall.

According to one embodiment, the stent of the invention includes a coating material. The coating material may be disposed continuously or discontinuously on the surface of the stent. Further, the coating may be disposed on the interior and/or the exterior surface(s) of the stent.

The coating material may include, but is not limited to a medicinal composition that leaches into the wall of a body lumen after implantation (e.g. to deliver a therapeutic agent to the body lumen). The coating is preferably a polymeric material, which is generally provided by applying to the stent a solution or dispersion of preformed polymer in a solvent and removing the solvent. Suitable polymeric coating materials, include, but are not limited to polytetraflouroethylene, silicone rubbers, or polyurethanes, all of which are known to be biocompatible. Non-polymeric material may alternatively be used.

In another aspect, the invention is directed to a delivery system for inserting stents into a body of a patient. In general, the delivery system includes a retractable sheath, a shaft partially disposed within the sheath and a rotatable locking element disposed over the sheath.

According to one embodiment, the retractable sheath has a wall of a flexible material and proximal and distal portions. As used herein, "distal" refers to an area or direction away from the medical operator inserting the device, while "proximal" refers to an area or direction close to the medical operator inserting the device into the patient. The retractable sheath defines an internal lumen that extends from the proximal to the distal portion. The internal lumen holds the stent in its collapsed state at the distal portion of the sheath. The sheath also defines a first groove and a longitudinal opening through the wall of the proximal portion. The first groove and longitudinal opening are connected and lie perpendicular to one another, forming an "L" or "T" shape.

Optional features of the sheath include a retraction handle, radiopaque locator bands, and a rounded distal end with a series of small longitudinal slits. The retraction handle may be disposed on the proximal portion of the sheath, and provides a grip to pull on to retract the sheath after insertion into a body of a patient. The radiopaque locator bands may be disposed on the wall of the sheath, and assist medical practitioners in positioning the stent under visualization by X-ray. The rounded distal end facilitates insertion of the stent in the urinary tract. The slits in the rounded distal end facilitate retraction of the sheath after insertion of the delivery system.

According to one embodiment, the shaft is coaxially disposed within the sheath and slidably movable within the lumen of the sheath. The shaft comprises at least one second groove. The shaft may further comprise an insertion handle, which provides a surface to push on to insert the delivery system into a body of a patient.

In a further embodiment, the rotatable locking element includes a tongue adapted to engage the first groove of the sheath and the at least one second groove of the shaft. The locking element is disposed over the proximal portion of the sheath.

When the tongue engages the first groove of the sheath and the at least one second groove of the shaft, relative movement between the sheath and the shaft cannot occur, thereby preventing premature deployment of the stent. To disengage the sheath from the shaft, the locking element is rotated, positioning the tongue in the longitudinal opening of the sheath. This allows relative movement between the shaft and the sheath, and thus allows retraction of the sheath over the shaft to deploy the stent. To disengage the tongue from the at least one second groove of the shaft, a thumb tab may be disposed on the locking element. Downward pressure on the thumb tab lifts the tongue out of the at least one second groove of the shaft. Releasing the tongue from the at least one second groove of the shaft allows the locking element to slide over the sheath.

The delivery system may include a slidable stop cup disposed on the sheath. The slidable stop cup is used to position the delivery system against the head of the penis of a male patient during insertion of the delivery system into the male urethra. Optionally, the slidable stop cup may be integrated with the locking element to stabilize or secure the positioning of the delivery system and the stent in the urinary tract.

In other aspects, the invention involves methods of placing stents, such as those previously described. One method of placing these and other collapsible and expandable stents into a body of a patient comprises collapsing the stent, inserting it into the distal portion of the sheath of the delivery system of the invention, inserting the delivery system into the body of the patient, retracting the sheath over the shaft, and removing the delivery system from the body of the patient, thereby deploying the stent within the body. An alternate method of placing the domed stent of the invention comprises providing the domed stent, positioning a conventional guidewire stylet assembly within the domed stent, inserting the guidewire stylet assembly into a body of a patient, and removing the assembly from the body of the patient, thereby deploying the domed stent within the body.

In another aspect, the invention involves methods for removing stents of the invention from a body of a patient after they have served their purpose. Removal of the stents of the invention comprises providing a cystoscope and a grasping device, inserting the cystoscope and grasping device into the body of the patient, locating the stent with the cytoscope, attaching the grasping device to the wall of the stent, removing the grasping device attached to the stent from the body, and removing the cystoscope from the body.

In yet another aspect, the invention involves methods of making the stents and delivery systems of the present invention. A method of making stents of the invention comprises injection molding the stent as one continuous piece. Alternatively, a method of making the domed stent comprises injection molding the body segment and proximal end segment in one mold, separately injection molding the dome in a second mold, and securing the individual components to one another. Similarly, a method of making the delivery systems of the invention comprises extruding the sheath, injection molding the other individual components and securing them together.

The foregoing and other objects, aspects, features, and advantages of the invention will become more apparent from the following description, the drawings, and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Stents, according to an illustrative embodiment of the invention, are useful for maintaining the patency of the prostatic urethra. Because the size and shape of this body lumen often varies from patient to patient, the stent is preferably sufficiently flexible to accommodate anatomical differences, while at the same time, sufficiently strong to maintain the prostatic urethra open in response to constrictive forces. Thus, according to the illustrative embodiment, stents of the present invention are therefore generally constructed of flexible biocompatible materials, including, but not limited to silicone, TEFLON® and other PTFE polymers, polyurethane polymers, thermal plastics or malleable metals. Such materials combine the rigidity necessary for maintaining the prostatic urethra open and able to pass fluids while also being soft enough for patient comfort. The flexible material of the stent may be doped with a radiopaque material to permit visualization by X-ray. Barium sulfate is one example of a suitable radiopaque agent that may be used with stents of the present invention.

According to a further feature, the stent of the illustrative embodiment is collapsible and expandable, and designed for use in the prostatic urethra of a male patient. Insertion of these and other collapsible and expandable stents into the patient may be accomplished by use of delivery systems according to the present invention, which comprise a retractable sheath, a shaft and a rotatable locking element.

Figure 1:
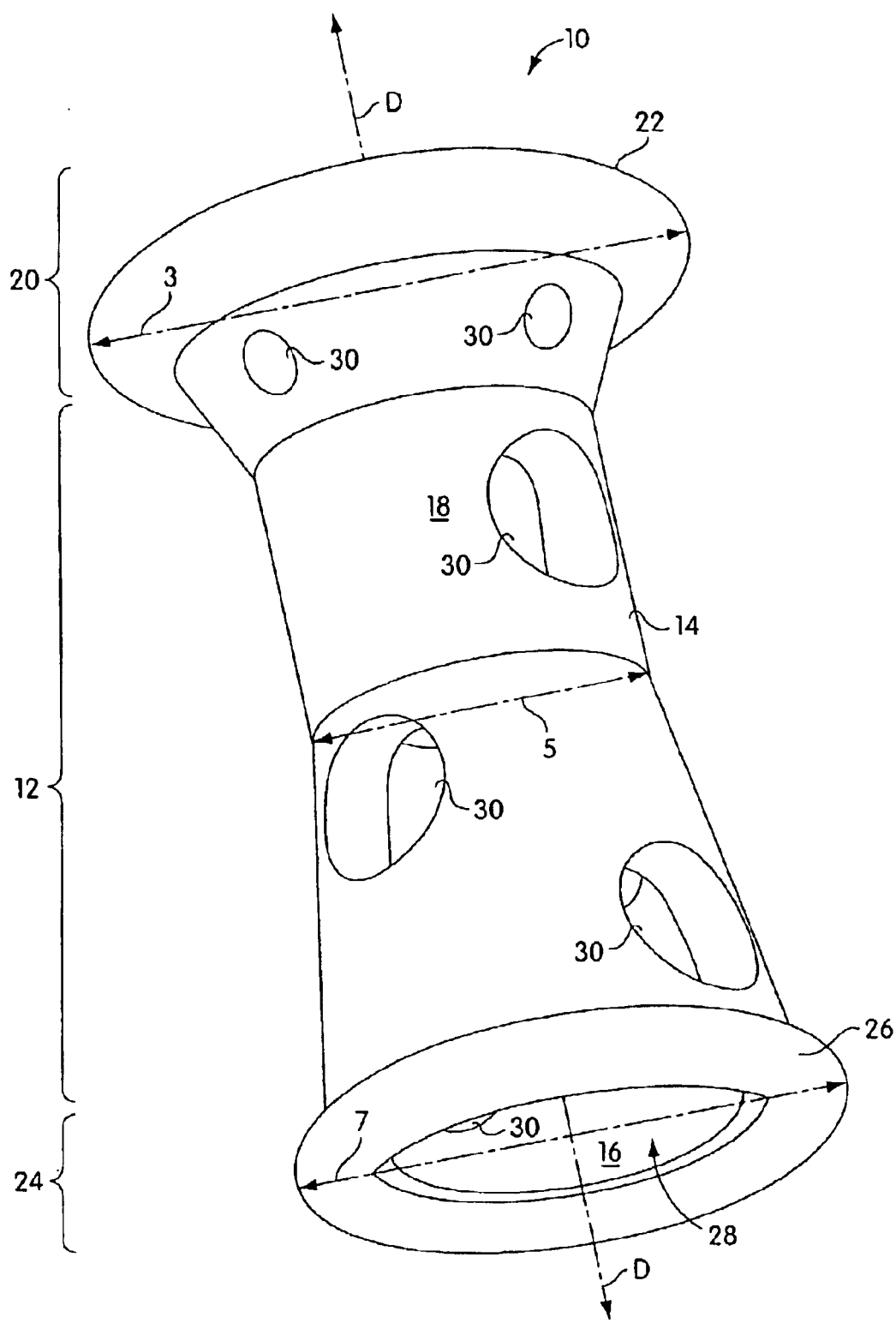
FIG. 1 is a perspective view of one embodiment of the stent of the invention with a double funnel configuration.

FIG. 1 depicts one illustrative embodiment of a stent 10. The stent 10 has a body segment 12 including a wall 14 made of a flexible material and extending between a first terminal end 20 and a second terminal end 24. The wall 14 has an internal surface 16 and an external surface 18. In the illustrative stent 10, the first terminal end 20 is wider than (e.g., has at least one external diameter greater than) at least some portion of the body segment 12 located between the first 20 and second 24 terminal ends.

In one illustrative embodiment, the first terminal end 20 includes a first retention ring 22 extending axially from the body segment 12. According to one feature, the first retention ring 22 anchors the stent 10 at the bladder end of the prostatic urethra, above the prostate, after insertion into a patient. In the illustrative stent 10, the second terminal end 24 is wider than (e.g. has at least one external diameter greater than) at least some portion of the body segment 12 extending between the first and second terminal ends, 20 and 24, respectively. Illustratively, the second terminal end 24 includes a second retention ring 26 extending axially from the body segment 12. According to one feature, the second retention ring 26 anchors the stent 10 at the external sphincter end of the prostatic urethra, below the prostate, after insertion into a patient. Additionally, the stent 10 may employ zero, one or two retention rings, such as the retention rings 22 and 26.

As skilled practitioners will appreciate, in other embodiments, only one of the terminal ends 20 and 24 may have an external diameter, such as diameter 3 or 7, that is greater than the external diameter, such as the diameter 5, of an intermediate portion of the body segment 12. In the illustrative stent 10, both the external cross-sectional diameters 3 and 7 of the terminal ends 20 and 24, respectively, are greater than the external cross-sections diameter 5 of an intermediate portion of location along the wall 14, between the first and second terminal ends 20 and 24. This configuration creates a funnel or hourglass shape to facilitate maintaining the stent 10 in position within the prostatic urethra. For example, in one illustrative embodiment, the diameter 5 of the body segment 12 is between about 18 French and about 21 French, while the diameters 3 and 7 of the first and second terminal ends 20 and 24, respectively, are between about 22 French and about 26 French. By varying the diameters 3, 5 and 7 and the length of the body segment 12, the stent 10 may be tailored to the individual needs of particular patients.

According to the illustrative embodiment, the stent 10 may also be designed according to the individual needs of particular patients in other ways. For example, the total length of the stent 10 may be varied between about 1.0 inch and about 2.5 inches, to accommodate the size of a patient's prostatic urethra, which varies in length from about 0.6 inches to about 3.0 inches. To determine the length of the patient's prostatic urethra, a conventional measuring catheter may be employed.

According to a further illustrative feature the diameters 3, 5 and/or 7 may be varied in size, relative to each other, to cause the wall 14 of the body segment 12 to be sloped at various angles. By way of example, for patients with wide prostatic urethras, the ratio of, for example, diameter 3 to diameter 5 may be made sufficiently large to cause the wall 14 to slope slopes sharply in an outward direction to ensure that the double funnel configuration anchors in place within the patient's body. The ratio between the diameter 7 and the diameter 5 may be similarly configured. In a further embodiment, for patients with narrower internal physiologies, the ratio of diameter 3 to diameter 5 and/or diameter 7 to diameter 5 may be selected to be small enough to avoid the potential discomfort associated with an ill-fitting stent, but large enough to anchor the stent 10 within the patient's body.

To provide drainage of fluid from a patient's bladder, a lumen 28 may extend through the body segment 12 between the first terminal end 20 and the second terminal end 24. Alternatively or additionally, drainage may be provided or enhanced by grooves located on the external surface 18 of the wall 14. Optionally, the wall 14 of the body segment 12 may define one or more through-holes 30 disposed along its length. Through-holes may also be disposed in the first and second terminal ends 20 and 24, respectively, or in the first and second retention rings 22 and 26, respectively.

Figure 2:
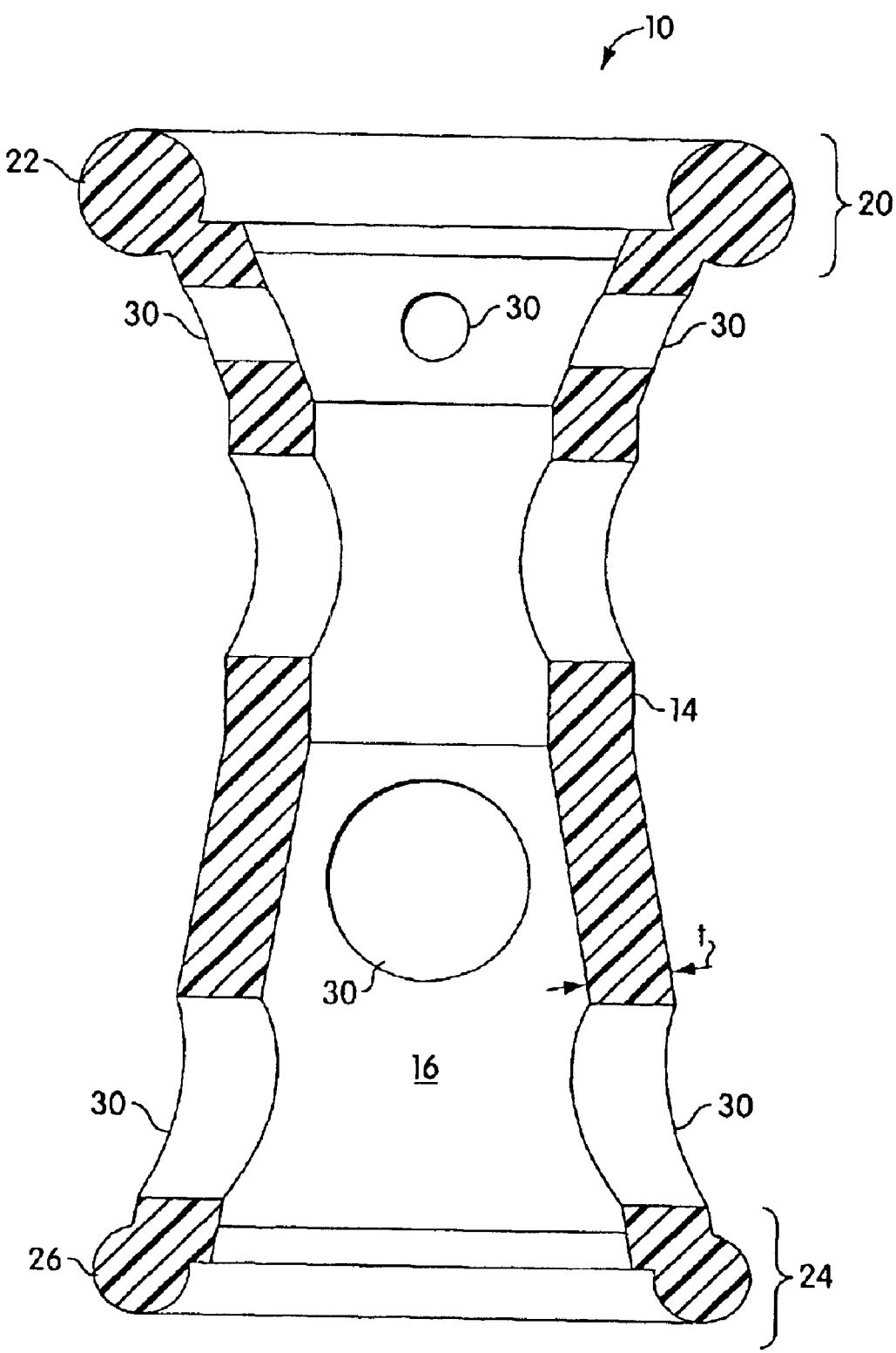
FIG. 2 is a longitudinal cross-sectional perspective view of the stent of FIG. 1.

The through-holes 30 extend through the external surface 18 to the internal surface 16 of the stent 10, and provide for fluid communication with the lumen 28 to facilitate urinary drainage. As illustrated in FIG. 2, the various through-holes 30 define openings through the wall 14 of the stent 10, shown in cross section. To avoid tissue in-growth and to maximize drainage, the diameter of the through-holes 30 in the disclosed embodiments is preferably between about 0.06 in. to about 0.12 in.

The thickness t and hardness h of the stent 10 affect its collapsible and expandable properties. If the stent 10 is too thick and/or too hard, the body segment 12 will not collapse to permit insertion into a patient's body. If the stent 10 is too thin and/or too soft, it may tear during or after insertion into a patient's body leading to potential medical complications. It may also fail to provide adequate support to the prostatic urethra. The thickness t, as shown in FIG. 2, is illustratively between about 0.01 in. and about 0.08 in. The hardness h is illustratively between about 35 shore A and about 65 shore A, with 50 shore A preferred.

Figure 3:
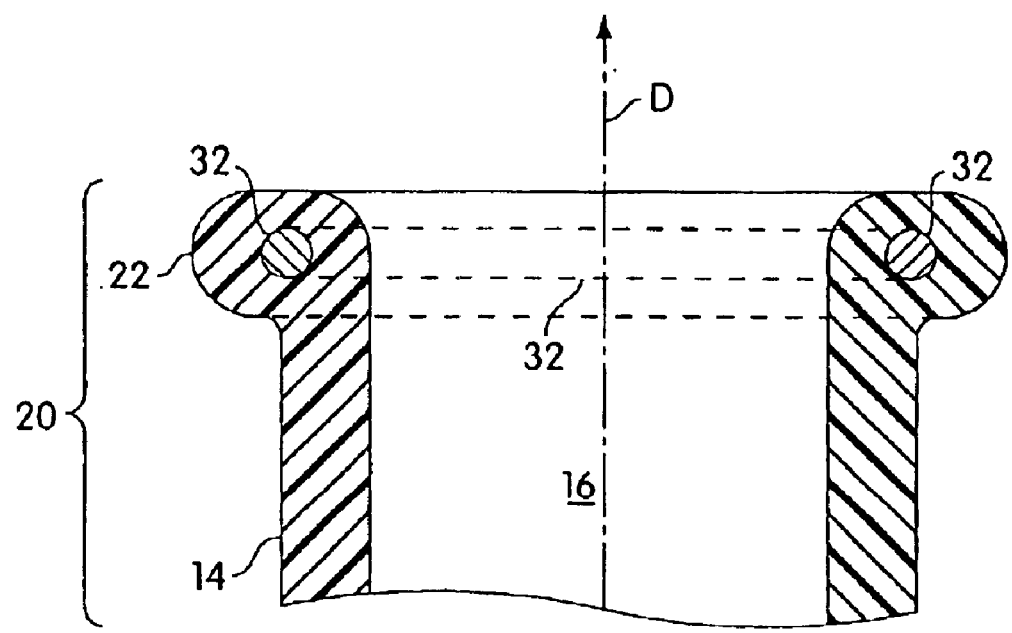
FIG. 3 is an enlarged longitudinal cross-sectional front view of the distal end segment of the stent of FIG. 1 with a portion of the elastic member shown in phantom line.

FIG. 3 shows a cross-sectional view of the first retention ring 22 extending axially from the first terminal end 22. In one embodiment, the first retention ring 22 is fabricated from the same flexible material as the body segment 12. As shown in FIG. 3, the illustrative first retention ring 22 includes an annular elastic member 32 to reinforce the first retention ring 22. The elastic member 32 may be embedded within the flexible material of the retention ring 22 or bound to a surface or groove of the first retention ring 22. Illustratively, FIG. 3 shows the elastic member 32 embedded within the first retention ring 22. According to the embodiment of FIG. 3, the elastic member 32 circumscribes the first retention ring 22.

The elastic member 32 may also be fabricated from a material having "superelastic" properties. Such a material may include alloys of In—Ti, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn. In the illustrative embodiment, the superelastic material includes a nickel and titanium alloy, known commonly as Nitinol® available from Memry Corp of Brookfield, Conn. or SMA Inc. of San Jose, Calif. The ratio of nickel and titanium in Nitinol® can vary. One preferred example includes a ratio of about 50% to about 56% nickel by weight. Nitinol® also possesses shape retention properties.

Figure 4:
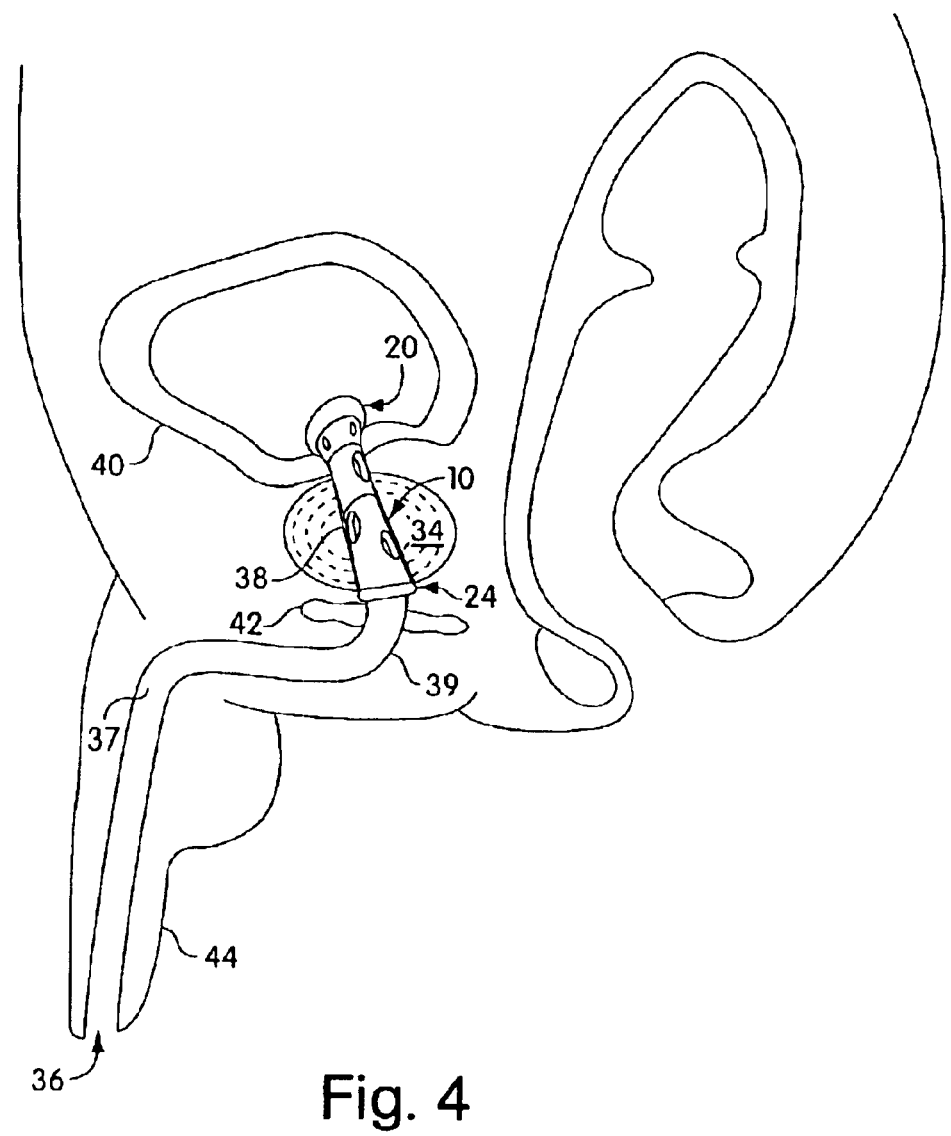
FIG. 4 is a cross-sectional view of the lower portion of the male abdomen illustrating a portion of the urinary tract with the stent of FIG. 1 positioned in the prostatic urethra.

FIG. 4 is a conceptual diagram depicting an illustrative placement of the stent 10 within a prostatic urethra 38 of a male patient. As seen in FIG. 4, the first terminal end 20 of the stent 10 rests above the prostate, at the bladder end of the prostatic urethra 38, while the second terminal end 24 of the stent 10 lies below the prostate, above the external sphincter 42. According to the illustrative embodiment, no part of the stent 10 extends through the external sphincter 42. Such positioning relative to the external sphincter 42 is preferable to avoid.

The details of the internal anatomy shown in FIG. 4 include the prostate gland 34, the urethra 36 (spanning from the penile urethra 37 through the bulbous urethra 39 and to the prostatic urethra 38), the bladder 40 and the external sphincter 42. The urethra 36 is the channel that conducts urine from the bladder 40 to the penis 44 for discharge from the body. The inside diameter of the urethra 36 is variable and may typically extend to about 0.8 in. The prostatic urethra 38 is a segment of the urethra 36 that tunnels through the prostate gland 34 and joins the prostate gland 34 to the urethra 36. Urine flows from the bladder through the prostatic urethra 36 to the bulbous urethra 39 and to the penile urethra 37 out of the body. The external sphincter 42 controls the flow of urine from the bladder 40.

Figure 5:
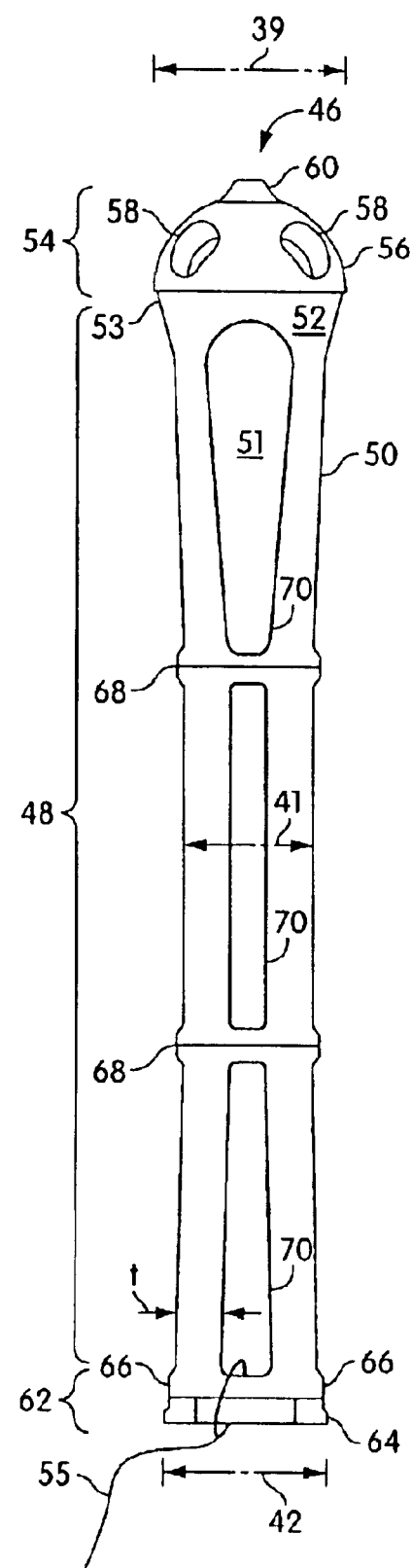
FIG. 5 is a side view of an alternate embodiment of the stent of the invention with a domed structure.

FIG. 5 depicts a stent 46 according to another illustrative embodiment of the invention. The stent 46 has a body segment 48. The body segment 48 is formed from a wall 50 of flexible material extending between a first terminal end 54 and a second terminal end 62. As shown in FIG. 5, the first terminal end 54 has external cross-sectional diameter 39. Similarly, the second terminal end 62 has an external cross-sectional diameter 43. The stent 46 also has at least one intermediate external cross-sectional diameter 41. According to the illustrative embodiment, both external diameters 39 and 43 are larger than the intermediate external diameter 41 to facilitate anchoring the stent 46 in place within the body of a patient. According to a further embodiment, a portion 53 of the body segment 48 located adjacent to the first terminal end 54 tapers to increase the cross-sectional diameter 39 of the first terminal end 54. Similarly, a portion 66 of the body segment 48 located adjacent to the second terminal end 62 flares to increase the cross-sectional external diameter 55 of the second terminal end 62. To further anchor the stent 46 in place within a patient's body, the second terminal end 62 includes a retention ring 64 extending axially from the body segment 48. Illustratively, the wall 50 has an external surface 52 and an internal surface (not shown) defining a lumen 51.

According to the illustrative embodiment of FIG. 5, the collapsible and expandable nature of the stent 46 is enhanced by annular collars 68, varying of the wall thicknesses t and providing at least one slot 70 disposed along the body segment 48. The annular collars 68 lie along various sections of the body segment 48 and serve as breaking points to radially collapse the stent 46. The wall thickness t of the body segment 48 decreases towards the annular collars 64. In one illustrative embodiment, the portion of the wall 50 that lies near the annular collars 64 has a t value of about 0.010 inches to about 0.30 inches with about 0.20 inches preferred. As the wall 50 extends away from the annular collars, the t value increases to between about 0.035 inches to about 0.055 inches, with about 0.04 in. preferred.

In one illustrative embodiment, the slots 70 are formed as concave inner or outer surfaces in the wall 50 of the body segment 48. In an alternative embodiment, the slots 70 are formed as through openings in the wall 50. In FIG. 5, the slots 70 are formed as through openings in the wall 50. These slots 70 enhance the collapsible properties of the stent 46. In addition, where the slots 70 are formed as concave surfaces, the surface area of the stent 46 is increased, allowing swollen prostate tissue to occupy these surfaces to further anchor the stent 46 in position within a body of a patient, without favoring encrustation of the stent 46. The size of the slots 70 is not confined to predetermined dimensions, but may vary, provided collapsibility is enhanced and the stent 46 retains an expandable structure. Optionally, a suture 55 may loop through a slot 70 defining an opening at the end segment 62 to facilitate removal of the stent 46.

According to a further feature, the first terminal end 54 includes a hollow dome 56 extending axially from the body segment 48. Rounded shoulders at the top of the dome 56 facilitate insertion of the stent 46 into small openings, such as the male urethra 36. The dome 56 includes at least one through-hole 58 adapted for urine transfer into the lumen 51.

The lumen 51 extends through the body segment 48 from the first 62 to the second end 54 to provide fluid communication between the at least one through-hole 58 and the urethra. Bodily fluid from the bladder drains into the at least one through-hole 58 residing in the dome 56 and into the body segment 48 to be released through the first terminal end 62 into the urethra.

Figure 6:
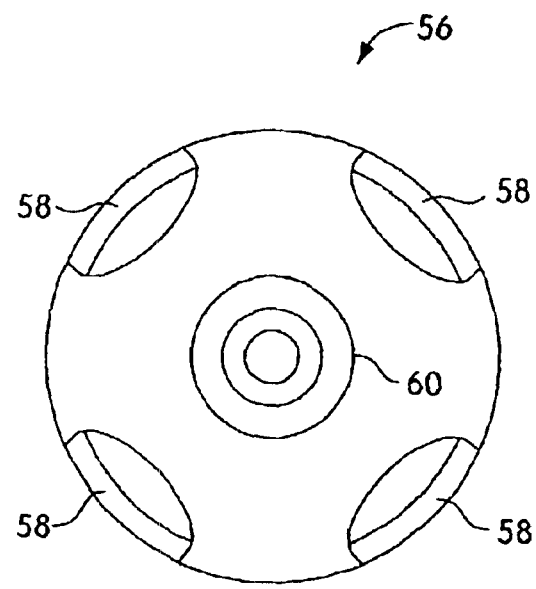
FIG. 6 is a top view of the embodiment of the stent of FIG. 5.

The dome 56, with its through-hole configuration, acts as a filter, allowing fluids and small harmless solid materials, such as blood clots, to pass, while preventing large blood clots and other solid materials, such as calculi or stone debris, from occluding the lumen and interrupting the passage of fluids through the stent 46. In one embodiment, the through-holes 58 have a diameter between about 0.06 inches and about 0.1 inches, with about 0.09 inches preferred. In one illustrative embodiment, the dome 56 includes two to six through-holes 58. In one particular embodiment, the dome 56 includes four through-holes. The through-holes may be disposed at various intervals (regular or irregular) along the surface of the dome. For example, FIG. 6 shows four through-holes 58 disposed at four different locations along the dome 56. In the illustrative embodiment of FIG. 6, the centers of the four through-holes 58 lie at 0°, 90°, 180°, and 270° angles along the periphery of the dome 56. The through-holes 58 may, however, lie at any combination of angles along the periphery of the dome 56.

Figure 7:
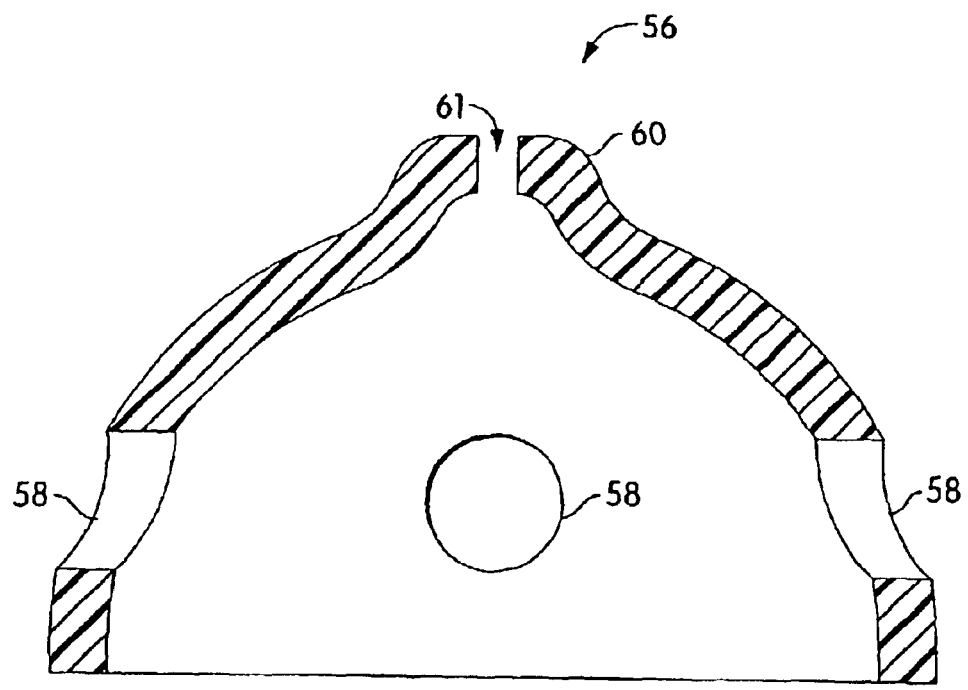
FIG. 7 is an expanded longitudinal cross-sectional view of the domed structure of the stent of FIG. 5.

As shown in FIGS. 5 and 6, the dome 56 may terminate in a protuberance 60, which facilitates insertion of the stent 46. The protuberance 60 is useful, for example, when the stent is inserted with a conventional guidewire stylet assembly, known to those of skill in the art. As seen in FIG. 7, the protuberance 60 may define a small lumen 61 for insertion of a guidewire through the stent 46. The lumen 61 of the protuberance 60 is preferably between about 0.039 inches and about 0.049 inches in diameter to accommodate conventional guidewires.

Figure 8A:
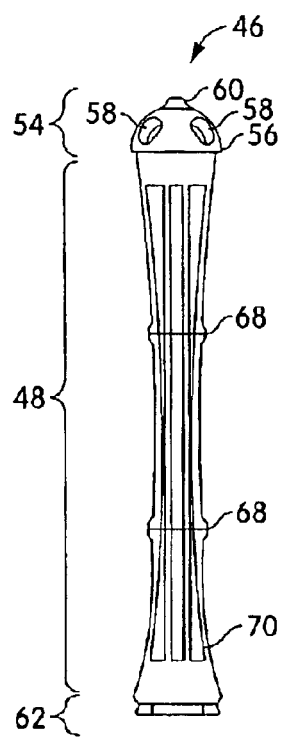
FIGS. 8A–8B are front views of stents according to the invention in two alternate collapsed states.
Figure 8B:
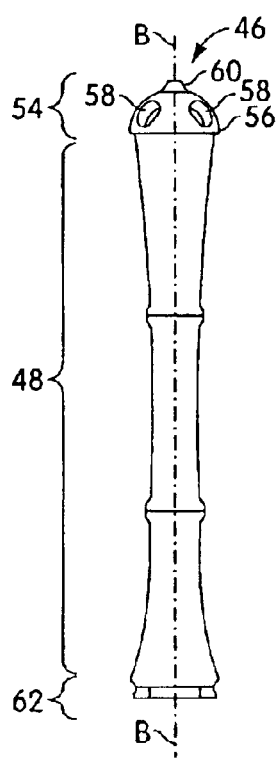

According to the illustrative embodiment of the invention, after the stents 10 and 46 have been collapsed, delivery systems of the invention may be used to introduce these and other collapsible/expandable stents into a body of a patient. FIGS. 8A–8B depict the domed stent 46 in its collapsed state in two possible configurations. In FIG. 8A, the wall 50 of the body segment 48 of the stent 46 is collapsed along the slots 70. In FIG. 8B, the stent 46 is folded in half on itself along line B—B.

Figure 9:
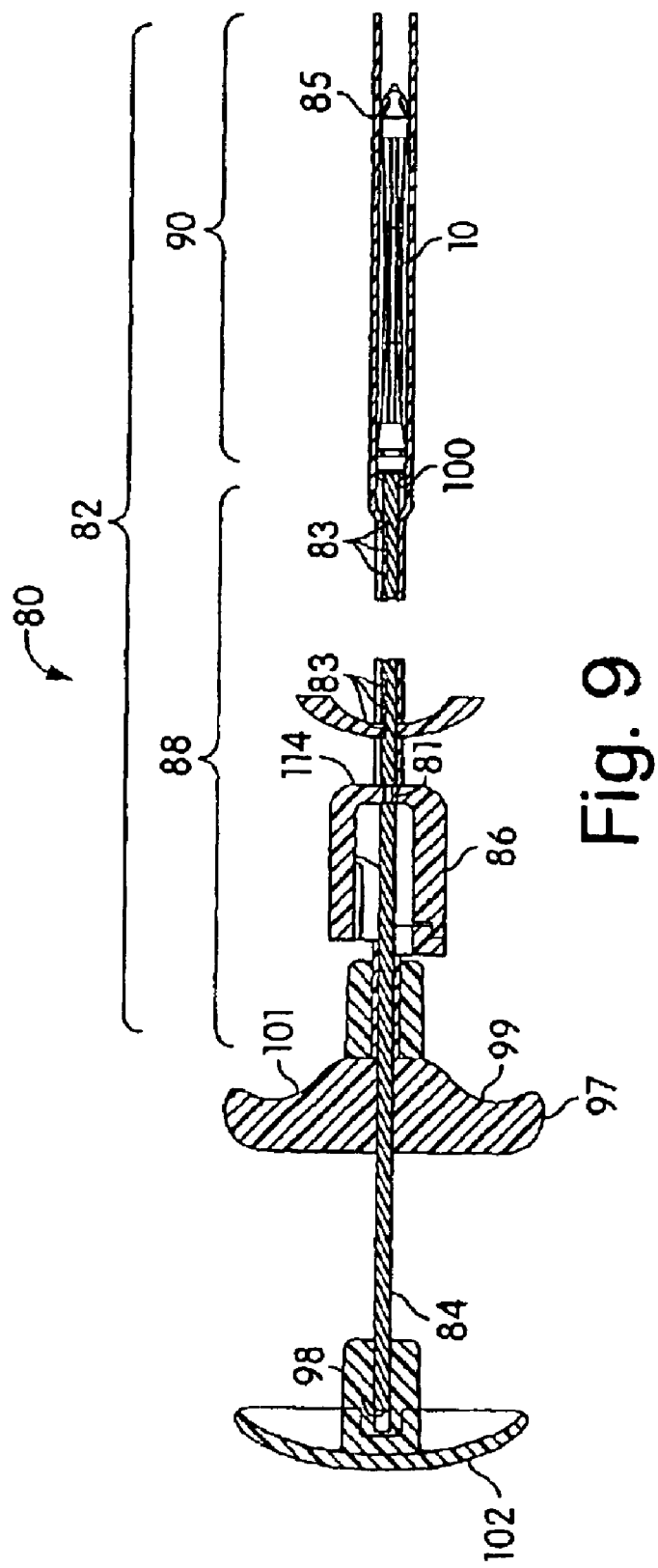
FIG. 9 is a longitudinal cross-sectional view of one embodiment of the delivery system according to the invention.

FIG. 9 shows one embodiment of a delivery system 80 used to introduce these and other collapsible and expandable stents into a body of a patient. In general, the delivery system 80 comprises a retractable sheath 82, a shaft 84, and a rotatable locking element 86.

The retractable sheath 82 has a proximal portion 88 and a distal portion 90. The sheath 82 defines an internal lumen that extends from the proximal portion 88 to the distal portion 90 for housing a portion of the shaft 84 and holding the stent 10. The sheath 82 further defines a first groove 81 transversal to the length of the sheath 82.

The retractable sheath 82 is made of a wall 85 of flexible material. Preferred flexible materials include, a high density polyethylene or a polypropylene based extrusion. According to the illustrative embodiment, the thickness of the wall 85 of the retractable sheath 82 is between about 0.050 inches and about 0.060 inches. According to one embodiment, the thickness of the wall 85 is about 0.055 inches. In one embodiment, the inner diameter of the sheath 82 is between about 0.280 inches and about 0.340 inches. According to one embodiment, the inner diameter of the sheath 82 is about 0.312 inches. According to a further embodiment the inner diameter of the sheath 82 is sized to accommodate the stent 10 in its collapsed state.

A retraction handle 97 may be disposed on the proximal portion 88 of the sheath 82. The retraction handle 97 is adapted to proximally retract the sheath 82. The retraction handle 97 may include two finger grips 99 and 101, which allow medical practitioners to more easily retract the sheath 82 by pulling back on the finger grips 99 and 101.

The shaft 84 includes a proximal end 98 and a distal end 100, and further includes at least one second groove 83. The at least one second groove 83 may be a notch limited to the top surface of the shaft 84, in which case the shaft 84 is rotatable with the locking element 86. Alternatively or additionally, the at least one second groove 83 may be a carved-out section of the shaft 84 that wraps circumferentially around the shaft 84 along a 90°, 180°, 270°, or 360° path, in which case the shaft 84 need not be rotatable.

The shaft 84 is preferably about 10 in. in length, and is preferably at least twice as long as the stent 10 being deployed. Thus, the length of the shaft 84 varies depending on the length of the stent 10 and the patient's internal anatomy. The distal end 100 of the shaft 84 may expand radially to form a plunger shape that abuts the stent 10.

Figure 10:
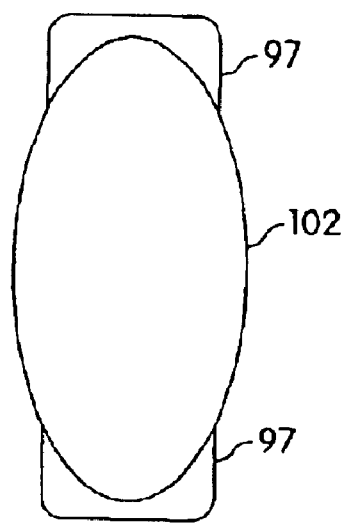
FIG. 10 is a side view of the delivery system of FIG. 9.

An insertion handle 102 may be disposed on the proximal end 98 of the shaft 84. The insertion handle 102 is adapted to insert the delivery system 80 into the body of a patient. FIG. 10 is a top view of the insertion handle 102 with the retraction handle 97 lying behind it in the background.

Figure 11:
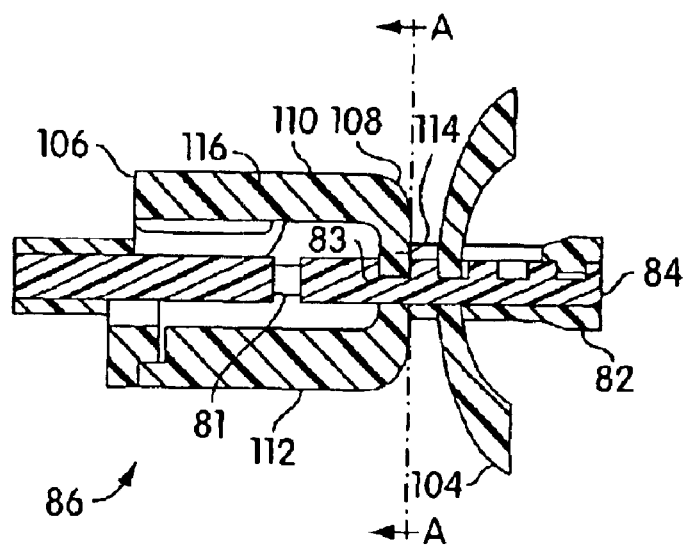
FIG. 11 is a partial longitudinal cross-sectional view of the slidable stop cup and the locking element engaging a portion of the sheath and a portion of the shaft of the delivery system.

The rotatable locking element 86 is disposed over the proximal portion 88 of the sheath, and comprises a tongue 114. The tongue 114 is adapted to engage the first groove 81 of the sheath 82 and the at least one second groove 83 of the shaft 84. Referring to FIG. 11, the illustrative locking element 86 includes a proximal end 106, a distal end 108, a top portion 110 and a bottom portion 112. In FIG. 11, the tongue 114 is disposed on the distal end 108 under the top portion 110 of the locking element 86, but may be positioned elsewhere on the locking element 86 provided it can engage both the first groove 81 of the sheath 82 and the at least one second groove 83 of the shaft 84. When the delivery system is in the locked position, the tongue 114 engages the first groove 81 of the sheath 82 and the at least one second groove 83 of the shaft 84. A more detailed view of the locking element 86 and its mode of operation is shown in FIGS. 12 and 13A–13C.

Figure 12:
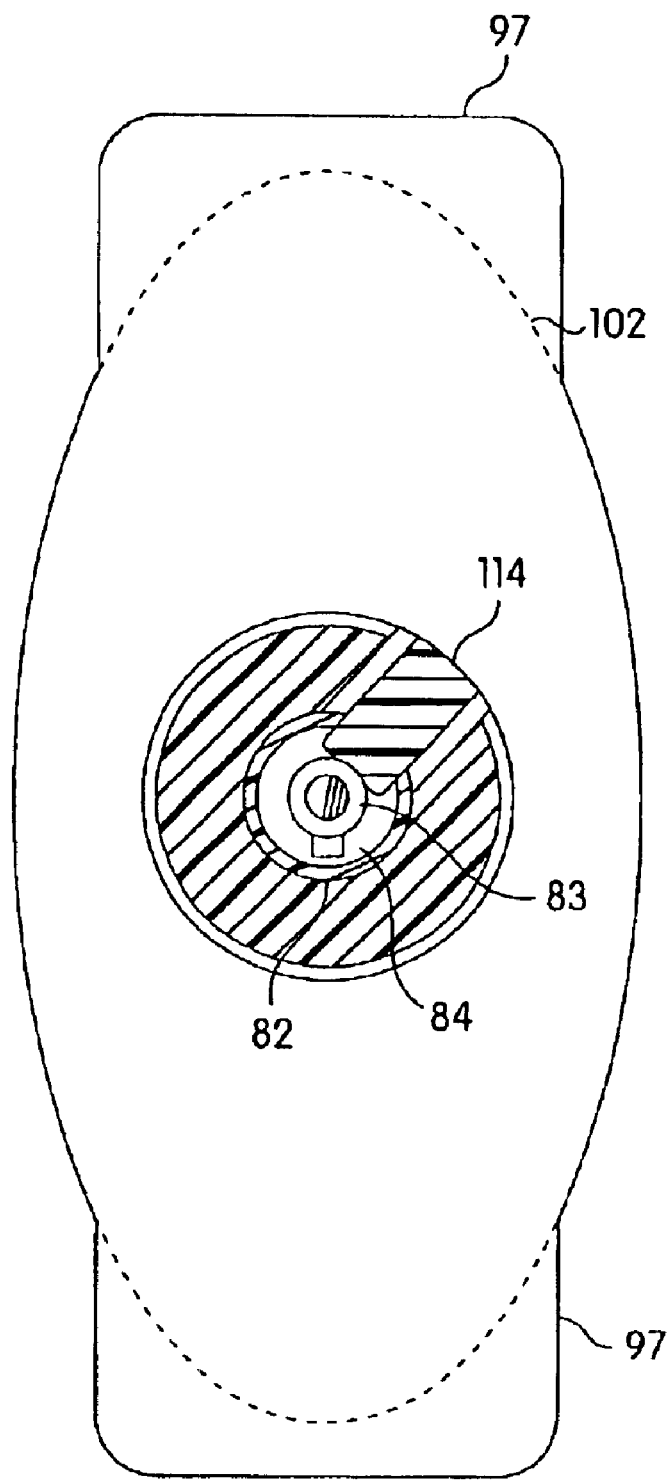
FIG. 12 is a transversal cross-sectional view of the locking element taken along line A—A of FIG. 11, with the insertion and retraction handles in the background.

FIG. 12 is a cross-sectional view of the distal end 108 of the locking element 86 taken along line A—A of FIG. 11. In FIG. 12, the tongue 114 is engaging the first groove 81 of the sheath 82 and the at least one second groove 83 of the shaft 84. This configuration prevents relative movement between the sheath 83 and the shaft 84 during insertion of the delivery system into a body of a patient. FIG. 12 also shows the insertion handle 102 and the retraction handle 97 in the background.

Figure 13A:
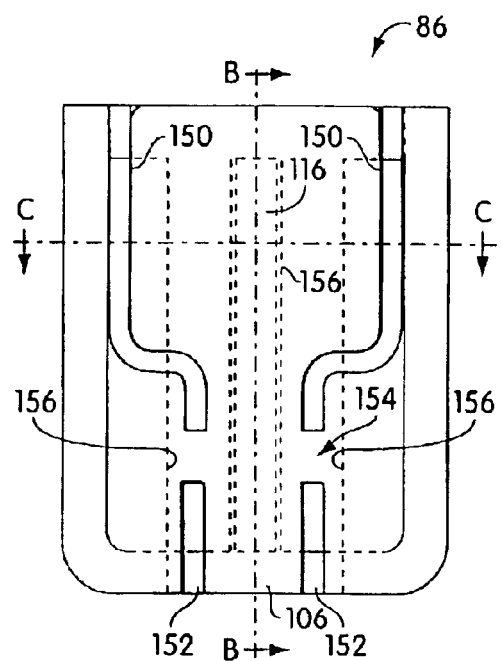
FIGS. 13A–13C show a front view (13A), a side view (13B), and a cross-sectional view (13C) of the locking element of the delivery system.

FIG. 13A is a front view of one embodiment of the locking element 86. In this embodiment, opposing "S" shaped slits 150 in the top surface of the locking element 86 define the thumb tab 116. The top surface of the locking element 86 further defines two longitudinal slits 152 that lie on either side of the tongue 106. A pivot point 154 sits between the "S" shaped slits 150 and the longitudinal slits 150, allowing a medical practitioner to lift the tongue 106 by depressing the thumb tab 116.

The locking element 86 may be reinforced with a series of ribs 156, which comprise areas of increased internal wall thickness. In FIG. 13A, the ribs 156 are shown in phantom. The ribs 156 provide added circumferential strength to the locking element 86 during rotation and engagement of the tongue 106.

Figure 13B:
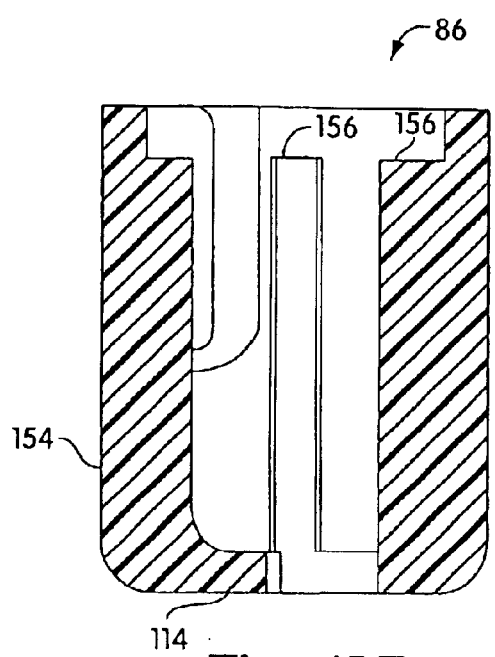

FIG. 13B is a side view of the locking element of FIG. 13A taken along line B—B. As shown more clearly in FIG. 13B, the ribs 156 comprise raised internal surfaces of the interior of the locking element 86. One of the ribs 156 reinforces the thumb tab and extends to the tongue 114.

Figure 13C:
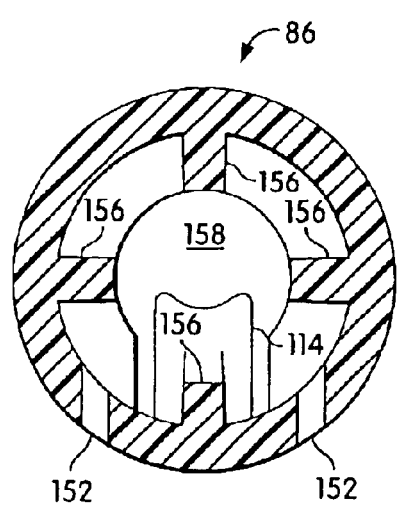

FIG. 13C is a cross-sectional view of FIG. 13A, taken along line C—C. In FIG. 13C, the ribs 156 lie at regular intervals in a quadrant configuration. The ribs 156 need not, however, lie at regular intervals or in any particular configuration, emphasis instead being placed on sufficient reinforcement for the locking element 86. FIG. 13C also shows the tongue 114 and the longitudinal slits 150. The central hole 158 that surrounds the tongue 114 of FIG. 13C allows the locking element 86 to slide over the shaft 84 after the tongue 114 is disengaged from the sheath 82 and shaft 84.

Figure 14:
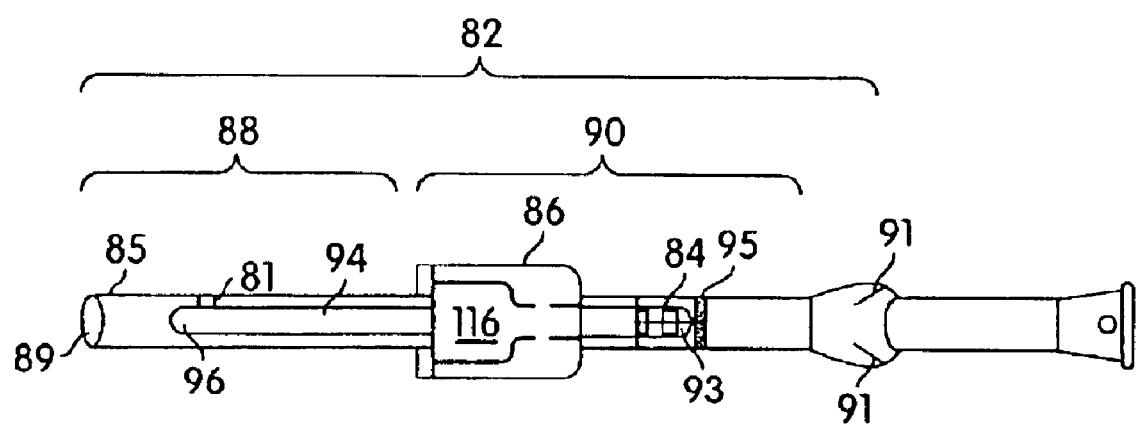
FIG. 14 is a partial side view of the delivery system showing the retractable sheath and the locking element of FIG. 9 and with the stent partially deployed.

After insertion of the delivery system into the body of the patient, the sheath 82 is withdrawn over the shaft 84 to deploy the stent 10. Referring to FIG. 14, a more detailed view of the structure of the retractable sheath 82 is provided. The retractable sheath 82 defines an internal lumen 89, which extends from the proximal portion 88 to the distal portion 90 and contains the stent 10 within the distal portion 90.

The retractable sheath 82 further defines the first groove 81 and a longitudinal opening 94 through the wall 85 of the proximal portion 88 of the sheath 82. The longitudinal opening 94 comprises a proximal end 96 and a distal end 93. The proximal end 96 of the longitudinal opening 94 is connected to and lies perpendicular to the first groove 81, forming an "L" or "T" shape. A portion of the shaft 84 may be seen through the distal end 93 and proximal end 96 of the longitudinal opening 94 of the sheath 82.

To disengage the tongue 114 from the first groove 81 of the sheath 82, the locking element 86 is rotated one-quarter turn clockwise to position the tongue 114 within the longitudinal opening 94 of the sheath 82, allowing relative movement between the sheath 82 and the shaft 84. FIG. 14 depicts the tongue 114 positioned within the longitudinal opening of the sheath 82. When the at least one second groove 83 is limited to a notch on the top surface of the shaft 84, rotation of the locking element 86, rotates the shaft 84 to maintain the tongue 114 within the at least one second groove 83 of the shaft 84. When the at least one second groove 83 of the shaft 84 wraps circumferentially around the shaft 84, rotation of the locking element 94 need not rotate the shaft 84 to maintain the tongue 114 within the at least one second groove 83, as the tongue 114 is merely re-positioned around the circumferential length of the same at least one second groove 83 of the shaft 84.

To facilitate insertion and withdrawal of the sheath 82 in and from the patient, the distal portion 90 of the sheath 82 may terminate in a rounded autramatic tip, which may comprise any number of slits 91 from two to six slits with four slits typical. The slits come together at the end of the rounded tip in a star-like configuration. The slits 91 facilitate proximal retraction of the sheath 82 by opening widely over the stent 10 during retraction over the shaft 84.

At least one radiopaque locator band 95 may be disposed on the wall 85 of the sheath 82. For example, two radiopaque locator bands 95 may be used to mark the stent 10 contained within the sheath 82 (such as shown in FIGS. 15A–D). Radiopaque locator bands 95 guide the medical practitioner (e.g. the physician) in positioning the stent 10 within a body of a patient under visualization by X-ray. The radiopaque locator bands 95 may be comprised of heavy metals, such as steel, tantulum, gold rings or the like.

In an alternate embodiment, a thumb tab 116 may be disposed between the proximal and distal ends 106 and 108 of the top portion 110 of the locking element 86 as shown in FIG. 11. The thumb tab 116 may be effaced within the profile of the locking element 86, or it may rise radially and outwardly at an angle with the tongue 114 to provide for greater pivoting angles to the tongue 114. Referring to FIG. 11, the tongue 114 of this embodiment is retractable from the grooves 83 of the shaft 84, and the locking element 86 is slidable along the length of the shaft 84. Downward pressure on the thumb tab 116 raises the tongue 114 out of the at least one second groove 83 of the shaft 84. This embodiment further comprises a slidable stop cup 104 disposed distal to the locking element 86 on the shaft 84. In addition, the grooves 83 comprise about 40–50 grooves spaced at approximately 10 grooves per in., spanning approximately half of the length of the shaft 84 at its distal end 100.

The locking element 86 may be used to distally advance the slidable stop cup 104 along the length of the shaft 84. After disengaging the tongue 114 from the first groove of the sheath 82 by rotating the locking element 86 to position the tongue 114 in the longitudinal opening 94, and disengaging the tongue 114 from the at least one second groove 83 by depressing the thumb tab 110, the locking element 86 becomes slidable along the length of the shaft 84.

The slidable stop cup 104 is used to position and stabilize the delivery system 80 against a body of a patient before deploying the stent 10. For example, after inserting the delivery system 80 into the prostatic urethra 38, the medical practitioner rotates the locking element 86, depresses the thumb tab 116, and slides the locking element 86 along the shaft 84 to advance the stop cup 104 along the shaft 84 until the stop cup 104 lies against the meatus in the head of the penis. At this point, the thumb tab 116 is released, re-engaging the tongue of the locking element 86 into one of the plurality of second grooves 83 of the shaft 84, thereby locking the slidable stop cup 104 in place. The tongue 106 does not, however, re-engage the first groove 81 of the sheath 82, but rather remains in the longitudinal opening 94 of the sheath 82 to allow relative movement between the sheath 82 and the shaft 84.

FIGS. 15A–15D illustrate a method of inserting a stent of the invention into the body of a patient with a delivery system of the invention. To load the stent 10 into the delivery system 80, manual or automated pressure is exerted on the body segment 12 and the proximal and distal end segments 20 and 24 of the stent 10 to collapse it (as in FIGS. 8A–B), and the collapsed stent 10 is placed within the sheath 82 through an opening in its proximal portion 88 or its distal portion 90. The collapsed stent 10, may be so placed by the manufacturer prior to sale, or by the medical practitioner prior to insertion.

Figure 15A:
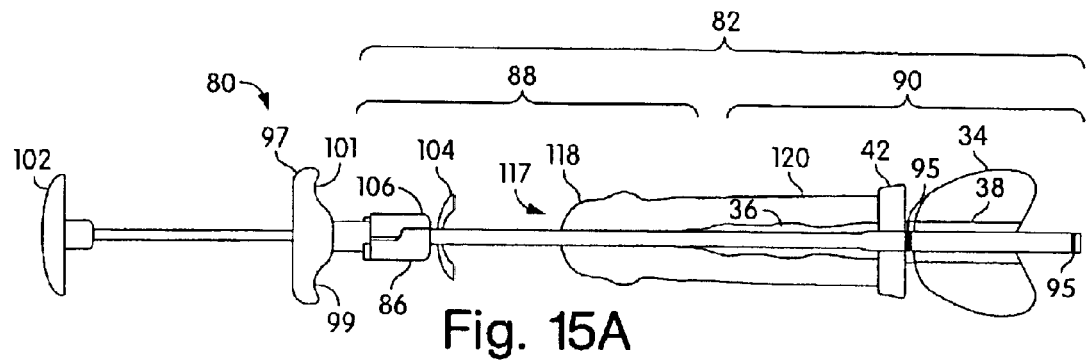
FIGS. 15A–15D illustrate a method for placing a collapsible/expandable stent into the prostatic urethra of a male patient using the delivery system of FIG. 9.

With the stent 10 in place, the delivery system 80, in its locked configuration, is introduced into the body of a male patient through the meatus 117 in the head 118 of the penis 120 into the urethra 36 as shown in FIG. 15A. In doing so, a medical practitioner may hold the head 118 of the penis 120 in one hand and exert pressure in a distal direction on the insertion handle 102 with the other hand. Under X-ray vision, the medical practitioner may use the radiopaque locator bands 95 to help position the delivery system 80 through the urethra, so that the distal portion 90 of the sheath 82, containing the two radiopaque locator bands 95, is located within the prostatic urethra 38 surrounded by the prostate gland 34 and above the external sphincter 42.

During insertion, the delivery system 80 is in its locked configuration to prevent premature deployment of the stent 10. The tongue 114 of the locking element 86 engages the first groove 81 of the sheath 82 and one of the plurality of grooves 83 of the shaft 84 to prevent relative movement between the sheath 82 and the shaft 84 (FIG. 11).

The locking element 86 may also be used to advance the slidable stop cup 104 against the head 118 of the penis 120. To position the slidable stop cup 104, the locking element 86 is rotated one-quarter turn clockwise to disengage the tongue 106 from the first groove 81 of the sheath 82, thereby positioning the tongue 106 in the longitudinal opening 94 of the sheath 82 (FIG. 14). The thumb tab 116 is then depressed, disengaging the tongue 106 from one of the plurality of grooves 83 of the shaft 84, so that the locking element 86 becomes slidably movable along the length of the shaft 84. This allows the medical practitioner to use the locking element 86 to distally advance the slidable stop cup 104 to the head 118 of the penis 120.

Figure 15B:
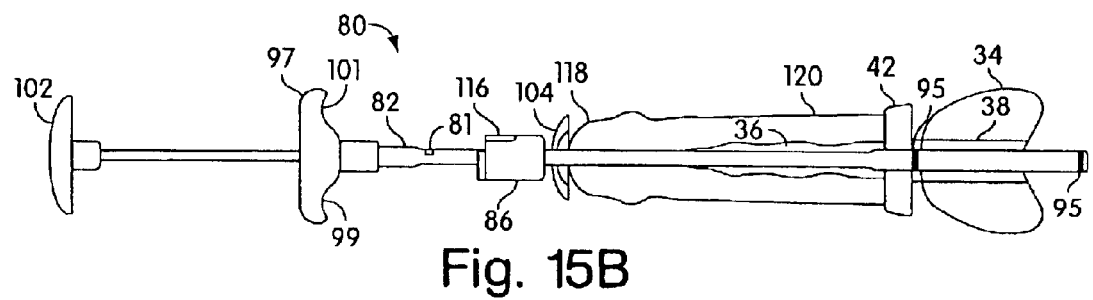

Referring to FIG. 15B, the locking element 86 has been advanced distally along the length of the delivery system 80 exposing the first groove 81 of the sheath 82, and positioning the slidable stop cup 104 at the head 118 of the penis 120. Once the slidable stop cup 104 is in this position, the thumb tab 116 is released, re-engaging the tongue 106 into another of the plurality of grooves 83 of the shaft 84, preventing movement of the slidable stop cup 104 backwards. The locking element 86 thereby maintains the slidable stop cup 104 against the head 118 of the penis 120, and secures the distal end 90 of the delivery system 80 within the prostatic urethra 38.

Figure 15C:
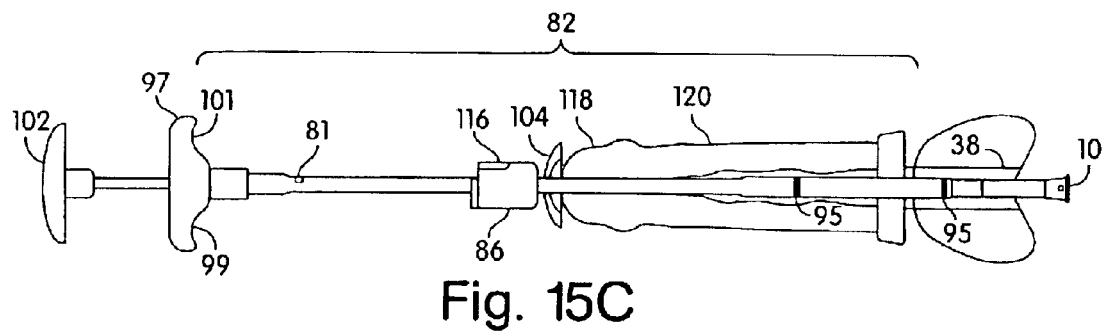

As FIG. 15C illustrates, after the slidable stop cup 104 is positioned against the head 118 of the penis 120, the sheath 82 is withdrawn, exposing and releasing the stent 10. To withdraw the sheath 82, the locking element 86 is rotated to position the tongue 106 within the longitudinal opening 94 of the sheath 82, allowing relative movement between the sheath 82 and the shaft 84. The medical practitioner then proximally withdraws the retraction handle 97 by positioning some fingers on the finger grips 99 and 101 and exerting pressure in a proximal direction. As the retraction handle 97 is slowly retracted, the sheath 82 moves backward, thereby partially deploying the stent 10 within the prostatic urethra 38 of the patient, as shown in FIG. 15C.

Figure 15D:
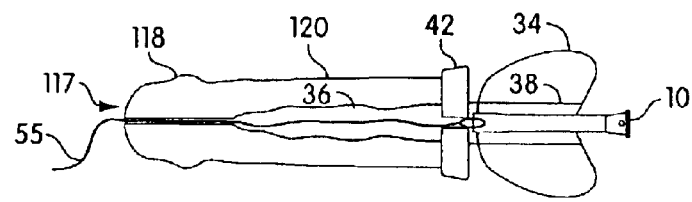

To fully deploy the stent 10 within the prostatic urethra 38, the sheath 82 is completely withdrawn over the stent 10 by the retraction handle 97, and the delivery system 80 is then removed from the body. Under these circumstances, the stent 10 reverts to its expanded geometry. FIG. 15D shows the expanded stent 10 deployed within the prostatic urethra 38 of the male patient, once released from the delivery system.

Figure 16:
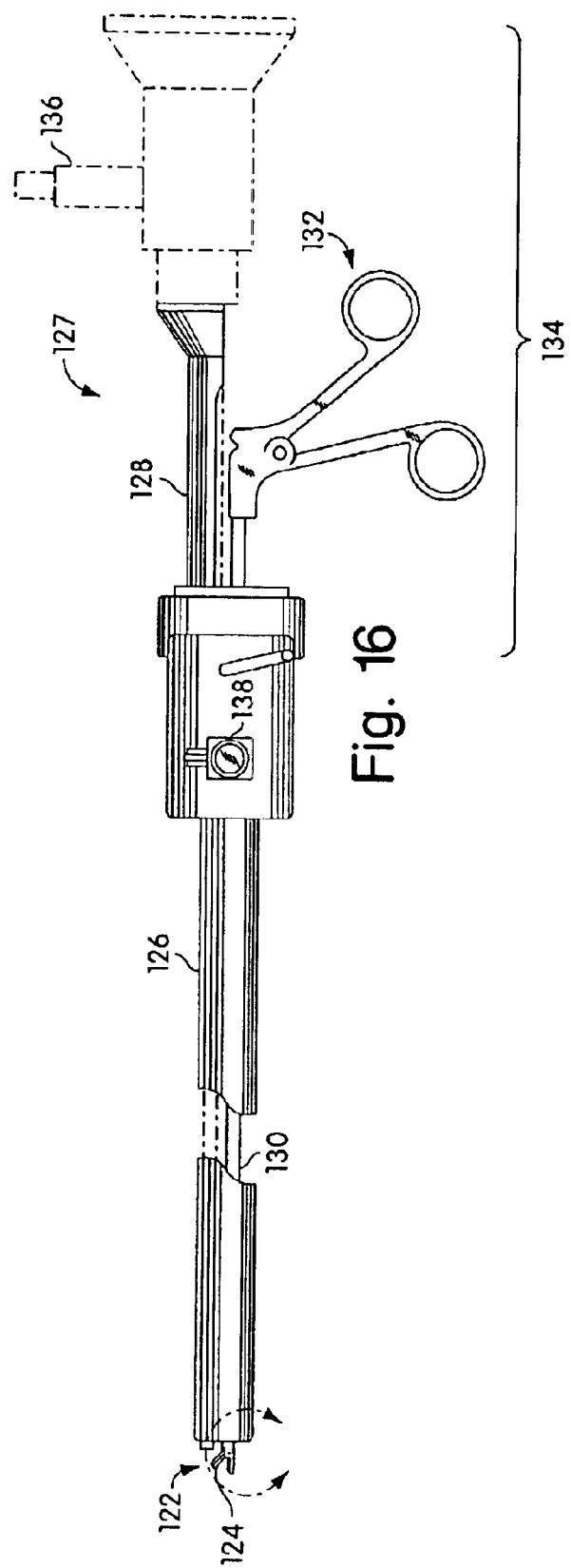
FIG. 16 is a side view of a cystoscope and grasping device extending through a sheath with a locking bridge attached to the sheath and a telescope in phantom line.
Figure 16A:
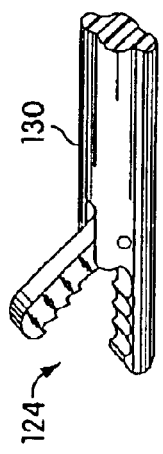
FIG. 16A is a blown-up view in perspective of the tip of the grasping device.

Once the stent has served its purpose, it is removed to avoid infection. Removal of the stent may be accomplished through use of a cystoscope and a conventional grasping device, shown in FIG. 16. FIG. 16 shows a grasping device 122 with forward forceps 124 disposed within a sheath 126 secured to a bridge 128 adapted to receive a cystoscope 127. A detail of the forward forceps 124 is illustrated in FIG. 16A.

In addition to the forward forceps 124, the grasping device 122 further comprises an axially elongated shaft 130 and scissors-like handles 132 disposed co-planar and at an angle with the elongated shaft 130 at a proximal portion 134 of the assembly. The scissors-like handles 132 are used to manipulate the forward forceps 124. The diameter of the sheath 126 must be large enough to accommodate the elongated shaft 130. The cytoscope 127 comprises a telescopic lens 136 for viewing a body lumen, and a port 138 for irrigating or draining the body lumen.

To remove stents of the invention from a body of a patient with the cytoscope grasping device assembly, a medical operator inserts the assembly into the urethra of the patient, locates the stent disposed within the prostatic urethra through the telescopic lens 136, manipulates the scissors-like mechanism 132 to close the forward forceps 124 on a wall of the stent, pulls the grasping device 122 proximally to remove the stent from the body of the patient, and removes the cystoscope 127 from the body.

Alternatively, removal of the stents of the invention may occur by proximally withdrawing the thread of suture material 55 (FIG. 5) until the stent 46 is pulled through the meatus of the head of a penis. As shown in FIG. 15D, the thread of suture material 55 is looped and threaded through an opening in the wall of the stent 10, and extends through the urethra to the exterior of the body where it can be easily grasped.

One illustrative method of manufacturing stents according to the illustrative embodiment of the invention (FIGS. 1 and 5) includes injection molding each stent of the invention as a single continuous piece or separately injection molding the various components, such as the dome and the body segment and securing these individual components together by suitable means, including but not limited to solder, weldment, or adhesive.

Injection molding includes providing an injection mold that profiles the different structural features of the stents, injecting liquid silicone or thermal plastic into the mold, allowing the mold to cure, and removing the cured structure from the injection mold. To provide an internal lumen, a core pin may be positioned down the center of the injection mold. The injection mold may further include protrusions extending from the inner surfaces of the mold for incorporating through-holes or slots into the stent. Alternatively, these features may be added to the stent after it is cured. To reinforce the stents with an elastic member, such as nitinol, the mold may incorporate the elastic member in the appropriate position, or the elastic member may be introduced through a small axial lumen incorporated into the mold after the stent is cured, or the elastic member may be taped or glued to the stent.

According to one embodiment, method of making the delivery system of the invention includes extruding the sheath, independently injection molding other individual parts, such as the shaft, locking element, slidable stop cup and insertion and retraction handles, and securing these individual parts together by suitable means, including but not limited to solder, weldment, or adhesive to assemble the delivery system.

Variations, modifications, and other implementations of what is described herein will occur to those of ordinary skill in the art without departing from the spirit and scope of the invention. Accordingly, the invention is to be defined not only by the preceding illustrative description.

What is claimed is:

1. A stent comprising, first and second terminal ends spaced apart from each other, at least one of the first and second terminal ends comprising a retention ring having an expanded ring state and a collapsed ring state, and a wall, disposed between the first and second terminal ends, and including an inner surface and an outer surface, the inner surface defining a lumen extending between the first and second terminal ends, and the outer surface having a substantially smooth portion, the wall having, a first outside cross-sectional diameter at the first terminal end, a second outside cross-sectional diameter at the second terminal end, at least one intermediate outside cross-sectional diameter at an intermediate location between the first and second terminal ends, each of the first and second outside cross-sectional diameters is greater than the intermediate outside cross sectional diameter and the outer surface of the wall tapers down from each of the first and second terminal ends to the at least one intermediate location, and an expanded state and a collapsed state, the wall being adapted to spontaneously revert from the collapsed state to the expanded state, wherein the retention ring is adapted to spontaneously revert from the collapsed ring state to the expanded ring state and, in the expanded ring state, the retention ring extends axially from the wall of the stent.

2. A stent according to claim 1 wherein the first terminal end of the stent is adapted for residing at a bladder end of a prostatic urethra of a patient and the second terminal end of the stent is adapted for residing at an external sphincter end of the prostatic urethra.

3. A stent according to claim 1 wherein the substantially smooth portion of the outer surface of the wall is adapted to inhibit tissue-in-growth.

4. A stent according to claim 1 wherein the retention ring includes an annular elastic core.

5. A stent according to claim 4 wherein the annular elastic core includes a nickel-titanium alloy.

6. A stent according to claim 1 wherein the first terminal end includes a retention ring, having an expanded ring state and a collapsed ring state, and being adapted to spontaneously revert from the collapsed ring state to the expanded ring state to facilitate retention of the retention ring within the bladder of the patient, and in the expanded ring state, the retention ring extending axially from the wall of the stent.

7. A stent according to claim 1 wherein the second terminal includes a retention ring, having an expanded ring state and a collapsed ring state, and being adapted to spontaneously revert from the collapsed ring state to the expanded ring state to inhibit the retention ring from passing through an external sphincter of the prostatic urethra of the patient, and in the expanded ring state, the retention ring extending axially from the wall of the stent.

8. A stent according to claim 1 wherein the first terminal end includes a first retention ring having a first expanded ring state and a first collapsed ring state and being adapted to spontaneously revert from the first collapsed ring state to the first expanded ring state to facilitate retention of the first retention ring within the bladder of the patient, the first retention ring extending axially from the wall of the stent in the first expanded ring state, and wherein the second terminal end includes a second retention ring having a second expanded second ring state and a second collapsed ring state and being adapted to spontaneously revert from the second collapsed ring state to the second expanded ring state to inhibit the second retention ring from passing through the external sphincter of the prostatic urethra of the patient, the second retention ring extending axially from the wall of the stent in the second expanded ring state.

9. A stent according to claim 1 wherein the wall further comprises at least one through aperture extending between the inner surface and the outer surface for providing fluid communication between the inner surface and the outer surface.

10. A stent according to claim 1 wherein the first outside cross-sectional diameter is greater than the second outside cross-sectional diameter.

11. A stent according to claim 1 wherein the second outside cross-sectional diameter is greater than the first outside cross-sectional diameter.

12. A stent according to claim 1, wherein the first terminal end comprises a domed segment having inner and outer surfaces and extending axially from the wall of the stent and adapted for facilitating insertion of the stent into the patient.

13. A stent according to claim 12 wherein the domed segment further comprises at least one through aperture extending radially between the inner and outer surfaces of the domed segment to provide fluid communication between the inner and outer surfaces of the domed segment.

14. A stent according to claim 13 wherein the domed segment further comprises an axially extending protuberance adapted for facilitating insertion of the stent into a patient.

15. A stent according to claim 14 wherein the axially extending protuberance has a through aperture sized to accommodate a guide wire.

16. A stent according to claim 1 wherein the wall of the stent includes a radio-opaque material.

17. A stent according to claim 1 wherein the wall comprises a coating.

18. A stent comprising, first and second terminal ends spaced apart from each other, at least one of the first and second terminal ends comprising a retention ring having an expanded ring state and a collapsed ring state, and a wall, disposed between the first and second terminal ends, and including an inner surface and an outer surface, the inner surface defining a lumen extending between the first and second terminal ends, and the outer surface having a substantially smooth portion, the wall having, a first outside cross-sectional diameter at the first terminal end, a second outside cross-sectional diameter at the second terminal end, at least one intermediate outside cross-sectional diameter at an intermediate location between the first and second terminal ends, wherein each of the first and second outside cross-sectional diameters is greater than the intermediate outside cross sectional diameter and the outer surface of the wall tapers down from each of the first and second terminal ends to the at least one intermediate location; and wherein, in the expanded ring state, the retention ring extends axially from the wall of the stent, and an expanded state and a collapsed state, the wall being adapted to spontaneously revert from the collapsed state to the expanded state.

19. A stent according to claim 18 wherein the first terminal end of the stent is adapted for residing at a bladder end of a prostatic urethra of a patient and the second terminal end of the stent is adapted for residing at an external sphincter end of the prostatic urethra.

20. A stent according to claim 18 wherein the substantially smooth portion of the outer surface of the wall is adapted to inhibit tissue-in-growth.

21. A stent according to claim 18 wherein the retention ring is adapted to spontaneously revert from the collapsed ring state to the expanded ring state.

22. A stent according to claim 21 wherein the retention ring includes an annular elastic core.

23. A stent according to claim 22 wherein the annular elastic core includes a nickel-titanium alloy.

24. A stent according to claim 18 wherein the first terminal end includes the retention ring adapted to spontaneously revert from the collapsed ring state to the expanded ring state to facilitate retention of the retention ring within the bladder of the patient.

25. A stent according to claim 18 wherein the second terminal includes the retention ring adapted to spontaneously revert from the collapsed ring state to the expanded ring state to inhibit the retention ring from passing through an external sphincter of the prostatic urethra of the patient.

26. A stent according to claim 18 wherein the wall further comprises at least one through aperture extending between the inner surface and the outer surface for providing fluid communication between the inner surface and the outer surface.

27. A stent according to claim 18 wherein the first outside cross-sectional diameter is greater than the second outside cross-sectional diameter.

28. A stent according to claim 18 wherein the second outside cross-sectional diameter is greater than the first outside cross-sectional diameter.

29. A stent according to claim 18 wherein the wall of the stent includes a radio-opaque material.

30. A stent according to claim 18 wherein the wall comprises a coating.

31. A stent comprising,
  a first terminal end including a first retention ring, the first retention ring having a first expanded ring state and a first collapsed ring state and being adapted to spontaneously revert from the first collapsed ring state to the first expanded ring state to facilitate retention of the first retention ring within the bladder of a patient;
  a second terminal end spaced apart from the first terminal end and including a second retention ring, the second retention ring having a second expanded second ring state and a second collapsed ring state and being adapted to spontaneously revert from the second collapsed ring state to the second expanded ring state to inhibit the second retention ring from passing through the external sphincter of the prostatic urethra of the patient; and
  a wall, disposed between the first and second terminal ends, and including an inner surface and an outer surface, the inner surface defining a lumen extending between the first and second terminal ends, and the outer surface having a substantially smooth portion, the wall having,
    a first outside cross-sectional diameter at the first terminal end;
    a second outside cross-sectional diameter at the second terminal end,
    at least one intermediate outside cross-sectional diameter at an intermediate location between the first and second terminal ends,
    wherein each of the first and second outside cross-sectional diameters is greater than the intermediate outside cross sectional diameter and the outer surface of the wall tapers down from each of the first and second terminal ends to the at least one intermediate location, and
    an expanded state and a collapsed state, the wall being adapted to spontaneously revert from the collapsed state to the expanded state,
  wherein, in the first expanded ring state, the first retention ring extends axially from the wall of the stent and, in the second expanded ring state, the second retention ring extends axially from the wall of the stent.

* * * * *